US012743652B2

(12) United States Patent
Boppana et al.

(10) Patent No.: US 12,743,652 B2
(45) Date of Patent: Sep. 22, 2026

(54) SYSTEMS AND METHODS FOR TRANSFORMING A USER INTERFACE ACCORDING TO PREDICTIVE MODELS

(71) Applicant: Evernorth Strategic Development, Inc., St. Louis, MO (US)

(72) Inventors: Adithya Chowdary Boppana, Dublin, OH (US); Adam M. Portik, Cranberry Township, PA (US); Pritesh J. Shah, Paramus, NJ (US); Christopher R. Markson, Hawthorne, NJ (US)

(73) Assignee: Evernorth Strategic Development, Inc., St. Louis, MO (US)

( * ) Notice: Subject to any disclaimer, the term of this patent is extended or adjusted under 35 U.S.C. 154(b) by 1184 days.

(21) Appl. No.: 17/392,682

(22) Filed: Aug. 3, 2021

(65) Prior Publication Data

US 2023/0050921 A1 Feb. 16, 2023

(51) Int. Cl.

| | |
|---|---|
| ***G06N 20/00*** | (2019.01) |
| ***G06F 16/23*** | (2019.01) |
| ***G06N 7/01*** | (2023.01) |
| ***G16H 70/40*** | (2018.01) |

(52) U.S. Cl.

CPC ......... *G06N 20/00* (2019.01); *G06F 16/2365* (2019.01); *G06N 7/01* (2023.01); *G16H 70/40* (2018.01)

(58) Field of Classification Search

CPC .......... G06N 20/00; G06N 7/01; G16H 70/40; G06F 16/2365

See application file for complete search history.

(56) References Cited

U.S. PATENT DOCUMENTS

| | | | |
|---|---|---|---|
| 9,974,453 | B2 | 5/2018 | Fonte |
| 10,169,715 | B2 | 1/2019 | Dirac |
| 10,453,456 | B2 | 10/2019 | Nicholls |
| 10,573,315 | B1 | 2/2020 | Nicholls |
| 10,621,491 | B2 | 4/2020 | Jonathan |

(Continued)

OTHER PUBLICATIONS

Rough, Kathryn, et al. "Predicting inpatient medication orders from electronic health record data." Clinical Pharmacology & Therapeutics 108.1 (2020): 145-154. (Year: 2020).*

(Continued)

*Primary Examiner* — Andrew T Chiusano
(74) *Attorney, Agent, or Firm* — Miller Johnson

(57) ABSTRACT

A computerized method for transforming a user interface according to machine learning includes selecting a persona and determining whether a first condition is true for an associated data structure. In response to determining the first condition is true, the method includes determining whether a second condition is true. In response to determining the second condition is not true, the method includes loading a first trained machine learning model, inputting a first set of explanatory variables to generate a first metric, and transforming the user interface according to the first metric. In response to determining the second condition is true, the method includes determining whether a third condition is true. In response to determining the third condition is true, loading a second trained machine learning model, inputting a second set of explanatory variables to generate a second metric, and transforming the user interface according to the second metric.

20 Claims, 13 Drawing Sheets

(56) References Cited

U.S. PATENT DOCUMENTS

| | | | | |
|---|---|---|---|---|
| 10,740,437 | B1 * | 8/2020 | Shannon | G16H 10/60 |
| 10,896,048 | B1 * | 1/2021 | Markson | G16H 70/40 |
| 11,515,022 | B1 * | 11/2022 | Dey | G16H 40/20 |
| 2009/0240528 | A1 * | 9/2009 | Bluth | A61B 5/6888<br>348/739 |
| 2017/0364640 | A1 * | 12/2017 | Badawi | G16H 50/20 |
| 2019/0094843 | A1 * | 3/2019 | Lee | G06N 5/04 |
| 2019/0196419 | A1 | 6/2019 | Wee | |
| 2019/0392295 | A1 | 12/2019 | Oi | |
| 2020/0058041 | A1 | 2/2020 | Bharwani | |
| 2020/0327444 | A1 | 10/2020 | Negi | |
| 2021/0056458 | A1 | 2/2021 | Savova | |
| 2022/0293233 | A1 * | 9/2022 | Sudharsan | G06N 5/04 |

OTHER PUBLICATIONS

Liu, Sicen, et al. “A hybrid method of recurrent neural network and graph neural network for next-period prescription prediction.” International Journal of Machine Learning and Cybernetics 11 (2020): 2849-2856. (Year: 2020).*

Jin, Bo, et al. “A treatment engine by predicting next-period prescriptions.” Proceedings of the 24th ACM SIGKDD international conference on knowledge discovery & data mining. 2018. (Year: 2018).*

Wright, Aileen P., et al. “The use of sequential pattern mining to predict next prescribed medications.” Journal of biomedical informatics 53 (2015): 73-80. (Year: 2015).*

Caroline Forsey, “Decision Trees: The Simple Tool That’ll Make You a Radically Better Decision Maker,” May 24, 2020, available at https://web.archive.org/web/20200524090215/https://blog.hubspot.com/marketing/decision-tree (Year: 2020).*

* cited by examiner

SYSTEMS AND METHODS FOR TRANSFORMING A USER INTERFACE ACCORDING TO PREDICTIVE MODELS

FIELD

The present disclosure relates to user interface adaptation and, more particularly, to transforming a user interface according to metrics generated by a trained machine learning model.

BACKGROUND

Currently, entities such as high-volume pharmacies offer drug management programs which may be implemented on local machines or via cloud-based servers. For example, a user who is a member of a pharmacy can create an account on a user device via a web portal to access the drug management program. Each user may be able to access the same information and may be presented with an identical user interface. Similarly, a support representative or an analyst working for the pharmacy may access information based on data structures generated for a user or a population of users via one or more user interfaces.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computerized method for transforming a user interface according to machine learning is presented. The method includes selecting a persona from a data store, loading, into a data processing module, a data structure associated with the selected persona, and determining, at the data processing module, whether a first condition is true for the data structure. In response to determining that the first condition is true for the data structure, the method may include determining whether a second condition is true for the data structure. In response to determining that the second condition is not true for the data structure, the method may include loading, at the data processing module, a first trained machine learning model and a first set of explanatory variables from the data structure, inputting, at the data processing module, the first set of explanatory variables to the first trained machine learning model to generate a first metric, and transforming the user interface according to the selected persona and the first metric.

The method may include, in response to determining that the second condition is true for the data structure, determining whether a third condition is true for the data structure. In response to determining that the third condition is true for the data structure, the method may include loading, at the data processing module, a second trained machine learning model and a second set of explanatory variables from the data structure, inputting, at the data processing module, the second set of explanatory variables to the second trained machine learning module to generate a second metric, and transforming the user interface according to the selected persona and the second metric. The first metric may be a probability of the persona transitioning from treatment with a single drug from a first class of drugs to multiple drugs from the first class of drugs within a first epoch.

In other features, the second metric may be a probability of the persona transitioning from treatment with a drug not containing a compound to a drug containing a compound within the second epoch. In other features, the first condition may be a presence of at least one drug of the first class of drugs in the data structure. In other features, the second condition may be a presence of more than one drug of the first class of drugs in the data structure. In other features, the third condition may be a presence of the compound in the data structure. In other features, the first trained machine learning model may be a first multiple logistic regression model. In other features, the second trained machine learning model may be a second multiple logistic regression model. In other features, the first class of drug may include drugs associated with treating pulmonary arterial hypertension. In other features, the compound may include prostacyclin.

A system for transforming a user interface according to machine learning is presented. The system may include a first data store, a second data store, and a processor operatively coupled to the first data store and the second data store. The first data store may include a persona and a data structure associated with the persona. The second data store may include at least one of a first trained machine learning model and a second trained machine learning model, and at least one of a first set of explanatory variables and a second set of explanatory variables. The processor may be configured by a set of instructions to determine whether a first condition is true for the data structure. In response to determining that the first condition is true for the first data structure, the processor may be configured by the set of instructions to determine whether a second condition is true for the data structure.

In response to determining that the second condition is not true for the data structure, the processor may be configured by the set of instructions to input the first set of explanatory variables into the first trained machine learning model and generate a first metric, and transform the user interface according to the first metric. In response to determining that the third condition is true for the data structure, the processor may be configured by the set of instructions to input the second set of explanatory variables into the second trained machine learning model to generate a second metric, and transform the user interface according to the second metric. The first metric may be a probability of the persona transitioning from treatment with a single class of drugs in a first class of drugs to treatment with multiple drugs in the first class of drugs within a first epoch.

In other features, the second metric may be a probability of the persona transitioning from treatment with a drug not containing a compound to treatment with a drug containing the compound within a second epoch. In other features, the first condition may be a presence of at least one drug of the first class of drugs within the data structure. In other features, the second condition may be a presence of more than one drug of the first class of drugs in the data structure. In other features, the second condition may be a presence of the compound in the data structure. In other features, the first trained machine learning model may be a first multiple logistic regression model. In other features, the second trained machine learning model may be a second multiple logistic regression model. In other features, the first class of drugs may include drugs associated with treating pulmonary arterial hypertension. In other features, the compound may be include prostacyclin.

A non-transitory computer-readable medium including executable instructions for transforming a user interface according to machine learning is presented. The executable instructions may include selecting a persona from a data store, loading, into a data processing module, a data structure associated with a selected persona, and determining, at the data processing module, whether a first condition is true for the data structure. In response to determining the first condition is true for the data structure, the executable instructions may include determining whether a second condition is true for the data structure. In response to determining the second condition is not true for the data structure, the executable instructions may include loading, at the data processing module, a first trained machine learning model and a first set of explanatory variables from the data structure, inputting, at the data processing module, the first set of explanatory variables to the first trained machine learning model to generate a first metric, and transforming the user interface according to the selected persona and the first metric.

In response to determining the second condition is true for the data structure, the executable instructions may include determining whether a third condition is true for the data structure. In response to determining the third condition is true for the data structure, the executable instructions may include loading, at the data processing module, a second trained machine learning model and a second set of explanatory variables from the data structure, inputting, at the data processing module, the second set of explanatory variables to the second trained machine learning model to generate a second metric, and transforming the user interface according to the selected persona and the second metric. The first metric may be a probability of the persona transitioning from treatment with a single class of drugs to treatment with multiple drugs in the first class of drugs within a first epoch.

In other features, the second metric may be a probability of the persona transitioning from treatment with a drug not containing a compound to treatment with a drug containing the compound within a second epoch.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

Introduction

Adapting a user interface based on metrics generated by a trained machine learning model provides a personalized user interface in an automated manner directly to a user. In various implementations, user interface adaptations based on the machine learning generated metrics can also be provided to support representatives and analysts. The machine learning generated metrics may be automatically determined by a bespoke machine learning model built and trained for the specific application.

In various implementations, the machine-learning model may be built and trained using data stored in a storage device of a pharmacy—for example, member data stored in the storage device of the pharmacy. The trained machine learning model may be used to determine one or more metrics by analyzing member data for a single member, or one or more populations of members.

Adapting a user interface for a support representative or an analyst provides a personalized user interface based on probability scores or data structures which may be generated from data related to one or more users and/or populations of users stored on a storage device. In various implementations, user interface adaptation based on the probabilities scores or data structures can also be provided to support representatives and analysts when using their respective devices. The probability scores or data structures may be generated based on data stored in a storage device of a pharmacy—for example, member data stored in the storage device of the pharmacy. Data specific to a user or group of users may be referred to as a persona.

Once determined, the machine learning generated metrics may be used to customize the user interface displayed to the user, analyst, and/or support representative. For example, based on the machine-learning generated metrics, a probability that a member will perform a certain action may be automatically calculated, and the user interface may be transformed to display the probability. In various implementations, probabilities that individual members within a given population will perform a certain action may be automatically calculated based on the machine learning generated metrics, and the user interface may be transformed to display the probabilities. In various implementations, the probabilities may be automatically formatted and sorted by machine before the user interface is transformed in order to improve overall ergonomics for the user, analyst, and/or support representative.

High-Volume Pharmacy

Figure 1:
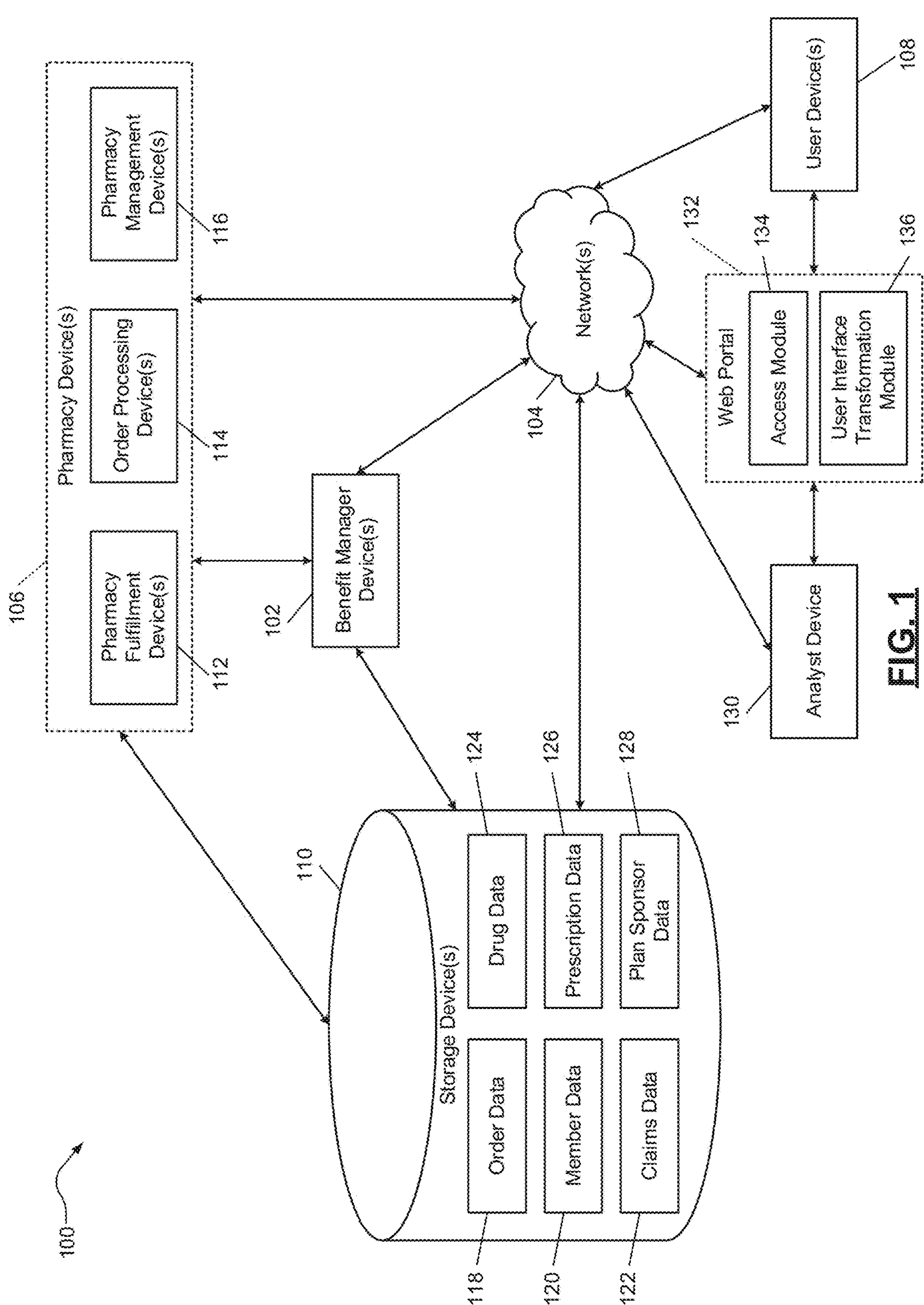
FIG. 1 is a functional block diagram of an example system including a high-volume pharmacy.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, support representative, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfillment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

In various implementations, the prescription drug history of the member data 120 may include information such as whether the member has been prescribed or received a specific class of drugs or drugs which have been used to treat a specific disorder within a first historical time period. For example, the prescription drug history may include data indicating whether the member has been prescribed or received drugs used to treat pulmonary arterial hypertension within the first historical time period. In various implementations, the prescription drug history may include data indicating whether the member has been prescribed or received drugs containing specific compounds, such as prostacyclin within the first historical time period. In various implementations, the first historical time period may be 30 about days, about 45 days, about 60 days, about 90 days, about 120 days, or about 365 days. In various implementations, the first historical time period may be about one month, about two months, about three months, about four months, about five months, about six months, about nine months, or about one year. In various implementations, the first historical time period may be in a range of about one day to about 365 days.

In various implementations, the member data 120 may include survey data, such as survey data indicative of whether the member experienced symptoms and a numerical rating of any symptoms the member may have experienced based on severity. For example, the symptoms may include shortness of breath upon exertion over a second historical time period, chest pains or palpitations over the second historical time period, shortness of breath at rest over the time period, shortness of breath upon exertion over the time period, and/or shortness of breath at rest over the second historical time period. In various implementations, the second historical time period may be about 30 days, about 45 days, about 90 days, about 120 days, or about 365 days. In various implementations, the second historical time period may be about one month, about two months, about three months, about four months, about five months, about six months, about nine months, about or one year. In various implementations, the second historical time period may be in a range of about one day to about 365 days.

In various implementations, the member data 120 may also indicate whether the member has been hospitalized since the member's last contact with the pharmacy. In various implementations, the member data 120 may include a member classification. For example, the member data 120 may indicate that the member is an integrated member, such as a member which is associated with the pharmacy as a pharmacy benefits manager. Alternatively, the member data 120 may indicate that the patient is a direct member, such as a member which is using the pharmacy for only a specific drug or class of drugs.

In various implementations, the member data 120 may also include data indicating whether the member has switched from monotherapy for pulmonary arterial hypertension to combination therapy within a given fourth historical time period. In various implementations, the fourth historical time period may be about 30 days, about 45 days, about 90 days, about 120 days, or about 365 days. In various implementations, the fourth historical time period may be about one month, about two months, about three months, about four months, about five months, about six months, about nine months, or about one year. In various implementations, the fourth historical time period may be in a range of about one day to about 365 days. In various implementations, the member data 120 may also include data indicating whether the member has switched from drugs which do not contain prostacyclin to one or more drugs that contain prostacyclin within the fourth historical time period.

In various implementations, the first historical time period, second historical time period, third historical time period, and fourth historical time period may be different from one another. In various implementations, one or more of the first historical time period, second historical time period, third historical time period, and fourth historical time period may be the same.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
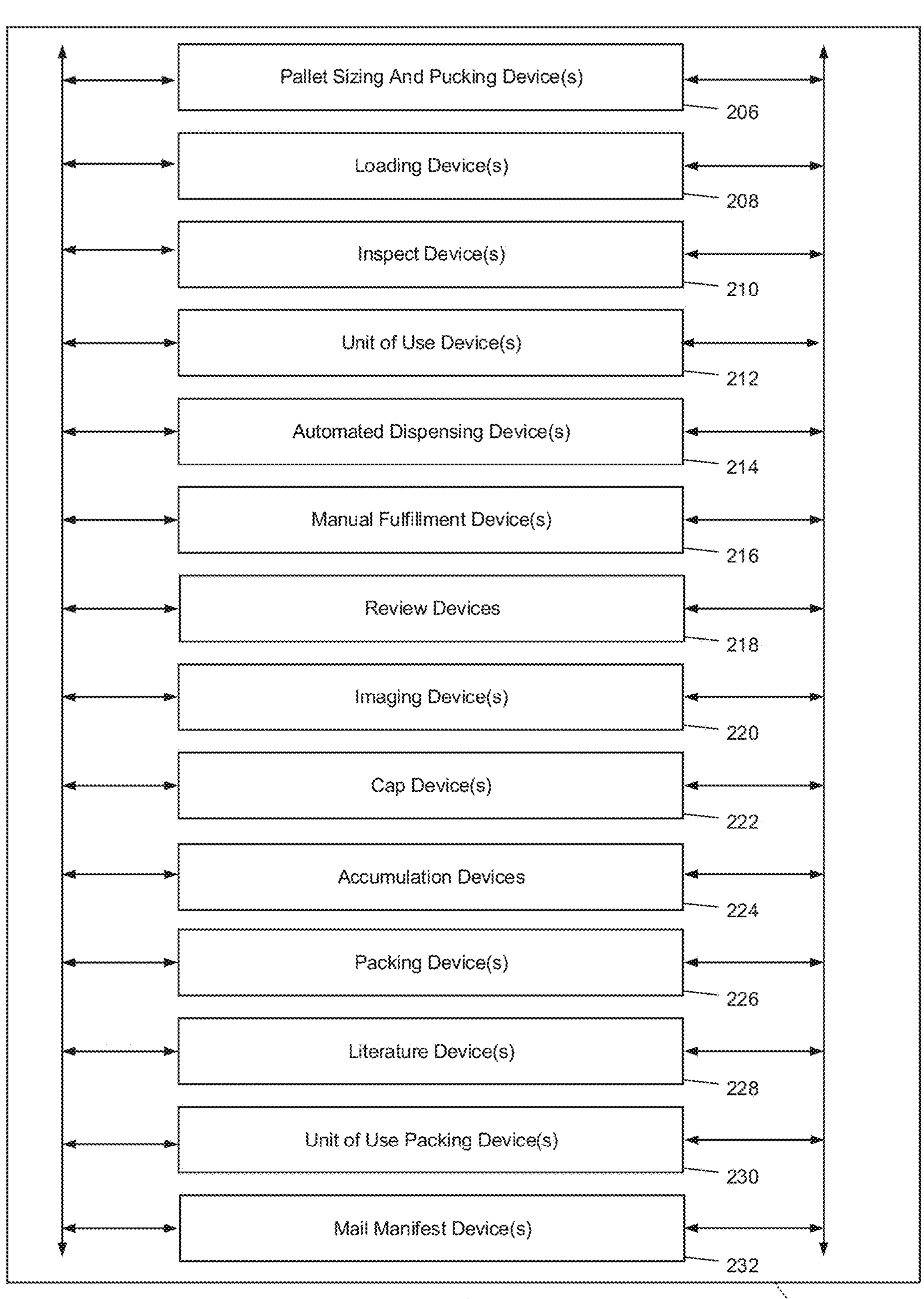
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device (s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
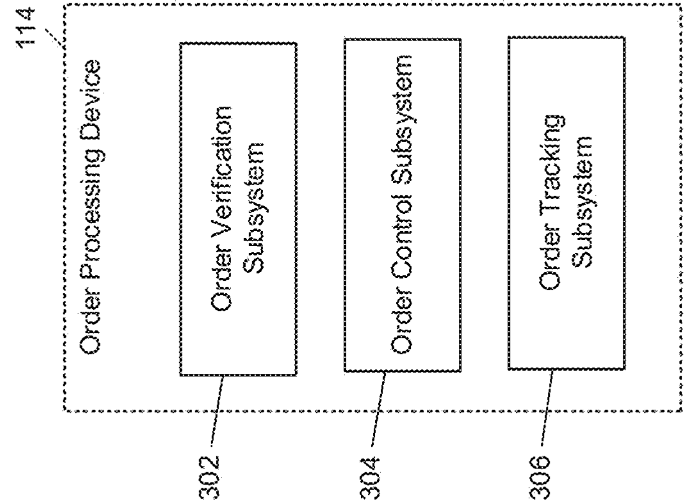
FIG. 3 is a functional block diagram of an example order processing device, which may be deployed within the system of FIG. 1.
Figure 3:

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Analyst Device and Web Portal

Referring back to FIG. 1, the system 100 may also include an analyst device 130. In various implementations, the analyst device 130 may communicate with other components of the system 100 directly or through a network, such as network 104. In various implementations, the system 100 may also include a web portal 132. The web portal 132 may include an access module 134 and a user interface transformation module 136. In various implementations, the web portal 132 may be hosted on a server on the network 104, and the user device 108 may communicate with the analyst device 130 through the network 104. In various implementations, the web portal 132 may be hosted on the analyst device 130, and the user device may communicate with the analyst device 130 directly. In various implementations, the user device 108 may submit a request to the access module 134. The access module 134 may communicate the request to the analyst device 130 and receive a response from the analyst device 130. The user interface transformation module 136 of the web portal 132 may transform a user interface at the web portal 132 according to the response from the analyst device 130. The access module 134 may then provide the user device 108 access to the transformed user interface.

Figure 4:
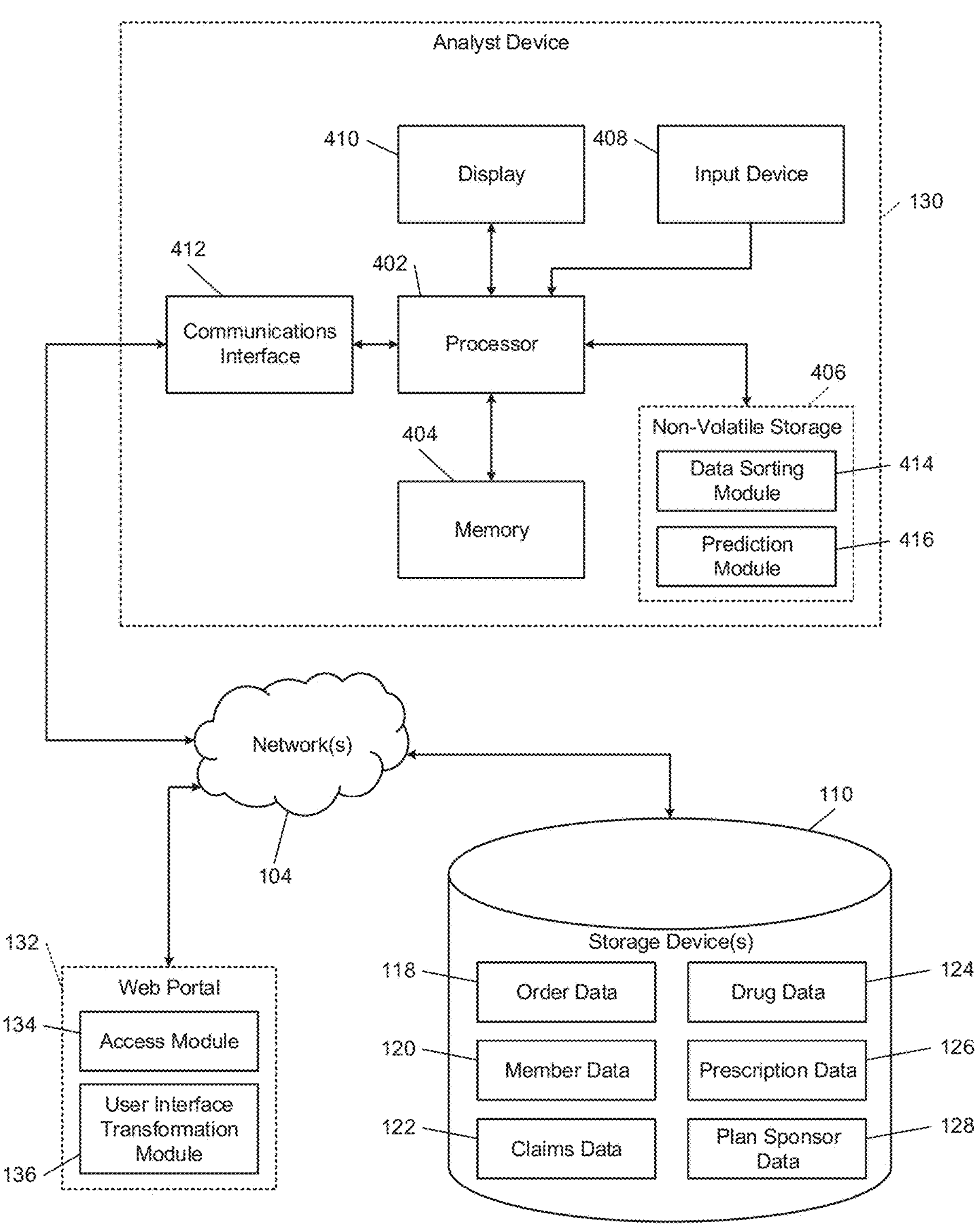
FIG. 4 is a functional block diagram of an example analyst device.

FIG. 4 is a functional block diagram of an example analyst device 130. The analyst device 130 may include a computer or a microprocessor. For example, the analyst device 130 may include a processor 402, volatile or non-volatile computer memory 404, such as random-access (RAM), and a non-transitory computer-readable storage medium, such as non-volatile storage 406. In various implementations, the non-volatile storage 406 may include a hard disk drive (HDD), single-level cell (SLC) NAND flash, multi-level cell (MLC) NAND flash, triple-level cell (TLC) NAND flash, quad-level cell (QLC) NAND flash, NOR flash, or any other suitable non-volatile memory or non-volatile storage medium accessible by the processor 402. The analyst device 130 may also include one or more input devices, such as input device 408, and one or more output devices, such as display 410. In various implementations, display 410 may be a touchscreen, and may also serve as an input device. In various implementations, the analyst device 130 may also include a transceiver, such as communications interface 412. In various implementations, the memory 404, non-volatile storage 406, input device 408, display 410, and/or communications interface 412 may be operatively coupled to the processor 402 and/or each other.

As illustrated in the example of FIG. 4, the processor 402 may communicate with the network 104 through communications interface 412. In various implementations, the processor 402 may access the storage device 110 and/or web portal 132 through the communications interface 412 and network 104, or directly through the communications interface 412. In various implementations, the non-volatile storage 406 may include a module for analyzing and binning members, and generating training datasets for machine learning, such as data sorting module 414. In various implementations, the non-volatile storage 406 may include a module for creating, training, and using machine learning models, such as prediction module 416. In various implementations, the data sorting module 414 and the prediction module 416 on the non-volatile storage 406 may access the storage device 110 through the processor 402, communications interface 412, and/or network 104. For example, the data sorting module 414 and the prediction module 416 may access the order data 118, member data 120, claims data 122, drug data 124, prescription data 126, and/or plan sponsor data 128.

In various implementations, the web portal 132 may access non-volatile storage 406 through the network 104, communications interface 412, and/or processor 402. For example, the access module 134 may access the data sorting module 414 and prediction module 416.

Data Sorting Module and Prediction Module

Figure 5:
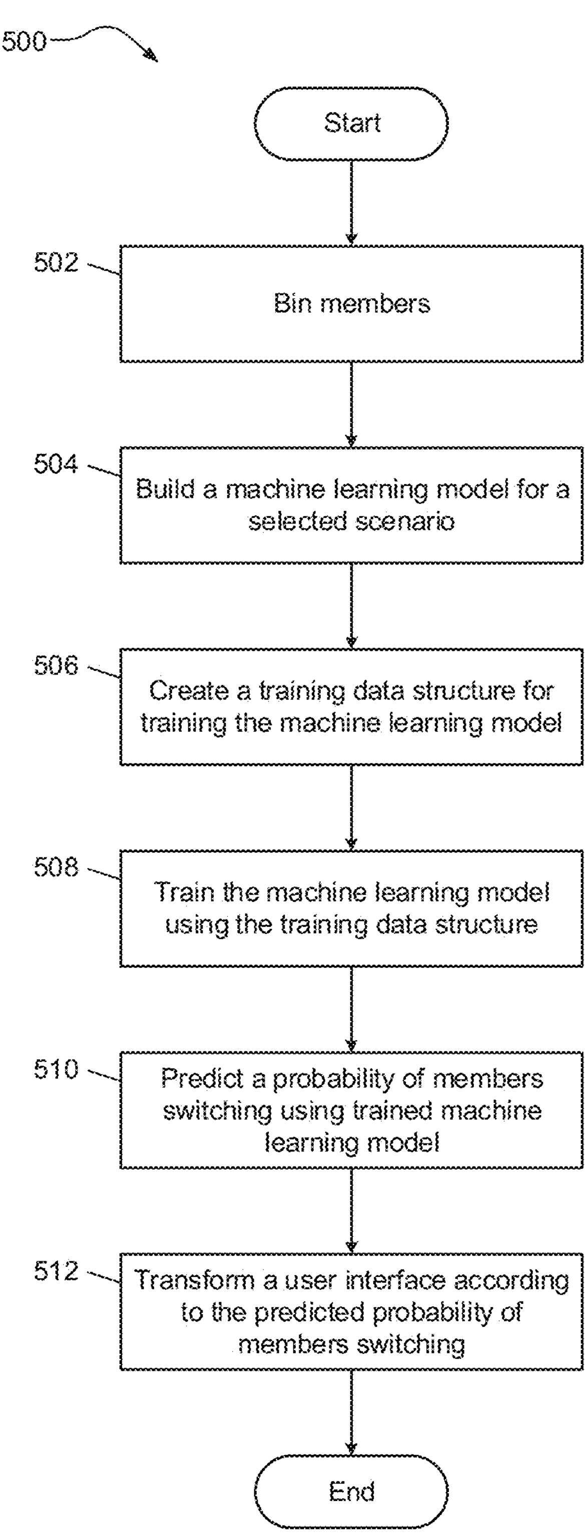
FIG. 5 is a flowchart of an example process according to the principles of the present disclosure.

FIG. 5 is a flowchart of an example process 500 which may be performed by the data sorting module 414 and/or the prediction module 416 of the non-volatile storage 406 of FIG. 4. Control, such as processor 402, may begin in response to a request received from the access module 134 of the web portal 132. In various implementations, control may begin in response to one or more scenarios. In a first scenario, control receives a request for a probability score of one or more members switching from a first form of therapy to a second form of therapy within a first epoch, such as a first targeted future time period. In various implementations, the first form of therapy may treatment with a single drug for pulmonary arterial hypertension ("monotherapy"), and the second form of therapy may be treatment with multiple drugs for pulmonary arterial hypertension ("combination therapy").

In a second scenario, control receives a request for a probability score of one or more members switching from treatment with drugs not containing a specific compound to treatment with one or more drugs containing the specific compound within a second epoch, such as a second targeted future time period. In various implementations, the specific compound may be prostacyclin. In various implementations, the first targeted future time period and/or the second targeted future time period may be about 30 days, about 45 days, about 60 days, about 90 days, about 120 days, or about 365 days. In various implementations, the first targeted future time period and/or the second targeted future time period may be about one month, about two months, about three months, about four months, about five months, about six months, about nine months, or about one year. In various implementations, the first targeted future time period and/or the second targeted future time period may be in a range of about one day to about 365 days. In various implementations, the first targeted future time period and/or the second targeted future time period may be the same or different. Throughout this description, the phrase "targeted future time period" may refer to either or both of the first targeted future time period or the second targeted future time period. While two discrete scenarios are provided as non-limiting examples, additional scenarios are also contemplated and may be implemented as appropriate.

Once the request is received, control proceeds to 502, where control accesses the data sorting module 414 to bin a population of members into one of several categories. For example, the data sorting module 414 may separate a population of members into a first bin of members which are not being treated for pulmonary arterial hypertension, a second bin of members which are undergoing monotherapy for pulmonary arterial hypertension, a third bin of members which are undergoing combination therapy for pulmonary arterial hypertension, a fourth bin of members which are being treated for pulmonary arterial hypertension with drugs which do not contain prostacyclin, and a fifth bin of members which are being treated for pulmonary arterial hypertensions with one or drugs which contain prostacyclin. In various implementations, the one or more bins may or may not overlap. After the members have been sorted into one or more bins, control transfers to 504.

At 504, control accesses the prediction module 416 to build a machine learning model appropriate to the request for a probability score. For example, if process 500 begins in response to the first scenario, the prediction module 416 builds an appropriate machine learning model for that scenario. If process 500 begins in response to the second scenario, the prediction module 416 builds an appropriate machine learning model for that scenario. After the machine learning model is built, control proceeds to 506.

At 506, control accesses the data sorting module 414 and/or the prediction module 416 to create a training data structure for training the machine learning model built at 504. After the machine learning model is built, control continues to 508. At 508, control accesses the prediction module 416 to train the machine learning model using the training data structure. After the machine learning model is trained, control continues to 510. At 510, control accesses the data sorting module 414 and/or prediction module 416 to predict a probability of members switching from one bin to another within the targeted future time period as appropriate to the scenario. For example, at 510, if under the first scenario, control may use the trained machine learning model to generate a probability of a single member switching from monotherapy to combination therapy within the targeted future time period. If under the second scenario, control may use the trained machine learning model to generate a probability of the single member switching from a drug not containing prostacyclin to a drug containing prostacyclin within the targeted future time period. In various implementations, control may use the trained machine learning model to generate a probability score for each member of a population of members. After the one or more probability scores are generated, control continues to 512.

At 512, control may access the user interface transformation module 136 to transform a user interface, such as at a user device 108, according to the one or more predicted probability scores. For example, if process 500 begins in response to control receiving a request for a probability score for a single member, the user interface transformation module 136 may transform the user interface of the user device 108 according to the probability score generated for the single member at 510. If process 500 begins in response to control receiving a request for a probability score for each of a population of members, the user interface transformation module 136 may transform the user interface of the user device 108 according to the probability score of each of the population of members. In various implementations, the user interface transformation module 136 may automatically parse and filter the probability scores for the population of members such that only members with scores above a targeted threshold are displayed.

Figure 6:
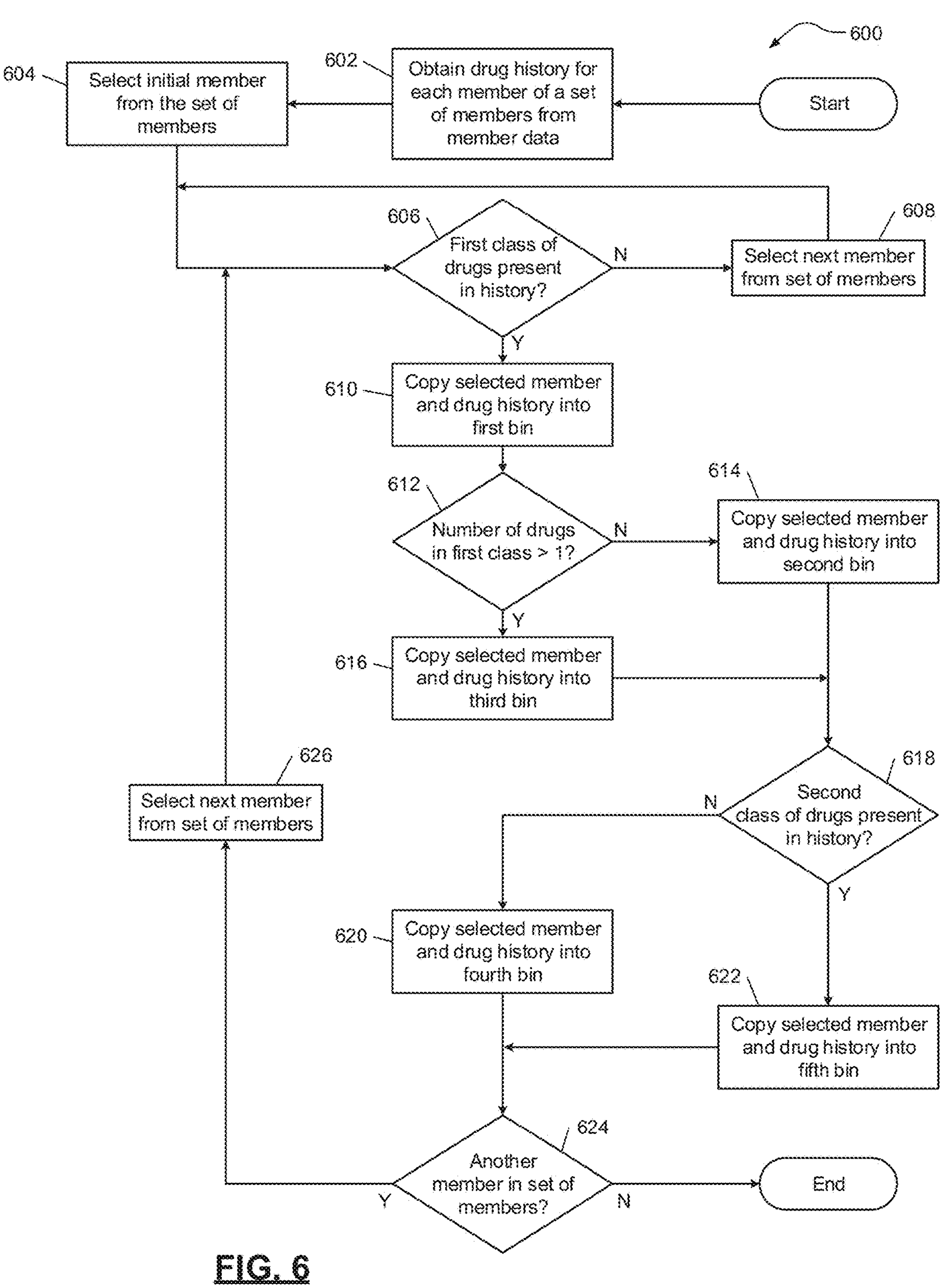
FIG. 6 is a flowchart of an example process for binning members.

FIG. 6 is a flowchart of an example process 600 which may be performed by the data sorting module 414 of FIG. 4 to bin members at step 502 of process 500 of FIG. 5. At 602, control obtains the drug history for each member of a population or set of members stored on the storage device 110, such as at the member data 120. The set of members may be the set of all members contained within the member data 120, or a specified subset of all members. In various implementations, control may obtain data such as the types and quantities of drugs prescribed to each member within the first historical time period. In various implementations, the drug history data may be associated with the respective member of the set of members and saved as a data structure.

In various implementations, the data structure may be stored on storage device 110 and/or non-volatile storage 406.

At 604, control accesses the data structure and selects the initial member from the set of members. After control selects the initial member, control proceeds to 606. At 606, control determines whether a first class of drugs is present in the drug history of the selected member. In various implementations, the first class of drugs may be any drug which may be used to treat a specific condition, such as pulmonary arterial hypertension. In various implementations, the first class of drugs may be any drug on a list of drugs stored on storage device 110 and/or non-volatile storage 406. For example, the first class of drugs may be any drug on a list of about 387,955 drugs which are related to treating pulmonary arterial hypertension. If at 606, control determines that no drug from the first class of drug is present in the drug history of the selected member, control proceeds to 608, where control selects the next member from the set of members and proceeds back to 606. If at 606, control determines that at least one drug from the first class of drugs is present in the drug history of the selected member, control proceeds to 610.

At 610, control copies the selected member and the drug history of the selected member into a first bin. The first bin may include the set of members being treated for pulmonary arterial hypertension. After the selected member has been added to the first bin, control proceeds to 612. At 612, control determines whether more than one drug from the first class of drugs is present in the drug history of the selected member. If at 612, control determines that more than one drug from the first class of drugs is not present in the drug history of the selected member (i.e., only one drug from the first class of drugs is present in the drug history), control proceeds to 614. At 614, control copies the selected member into a second bin. The second bin may include the set of members being treated for pulmonary arterial hypertension with monotherapy. Control then proceeds to 618. If at 612, control determines that more than one drug from the first class of drugs is present in the drug history of the selected member, control proceeds to 616, where control copies the selected member into a third bin. The third bin may include the set of members being treated for pulmonary arterial hypertension with combination therapy. Control then proceeds to 618.

At 618, control determines whether a second class of drugs is present in the drug history of the selected member. For example, the second class of drugs may be drugs containing prostacyclin. If at 618, control determines that at least one drug from the second class of drugs is not present in the drug history of the selected member, control proceeds to 620. Otherwise, if at 618, control determines that at least one drug from the second class of drugs is present in the drug history of the selected member, control proceeds to 622. At 620, control copies the selected member into the fourth bin and proceeds to 624. The fourth bin may include the set of members currently not being treated with drugs containing prostacyclin. At 622, control copies the selected member into the fifth bin and proceeds to 624. The fifth bin may include the set of members currently being treated with one or more drugs containing prostacyclin.

At 624, control determines whether there is another member which has not yet been analyzed is present in the set of members within the data structure stored on storage device 110 and/or non-volatile storage 406 at step 602. If at 624, control determines that another member that has not yet been analyzed is present in the set of members, control proceeds to 626, where control selects the next member from the set of members and proceeds to 606. If at 624, control determines that another member that has not yet been analyzed is not present in the set of members (i.e., each member of the set of members has been analyzed), control ends process 600.

Figure 7:
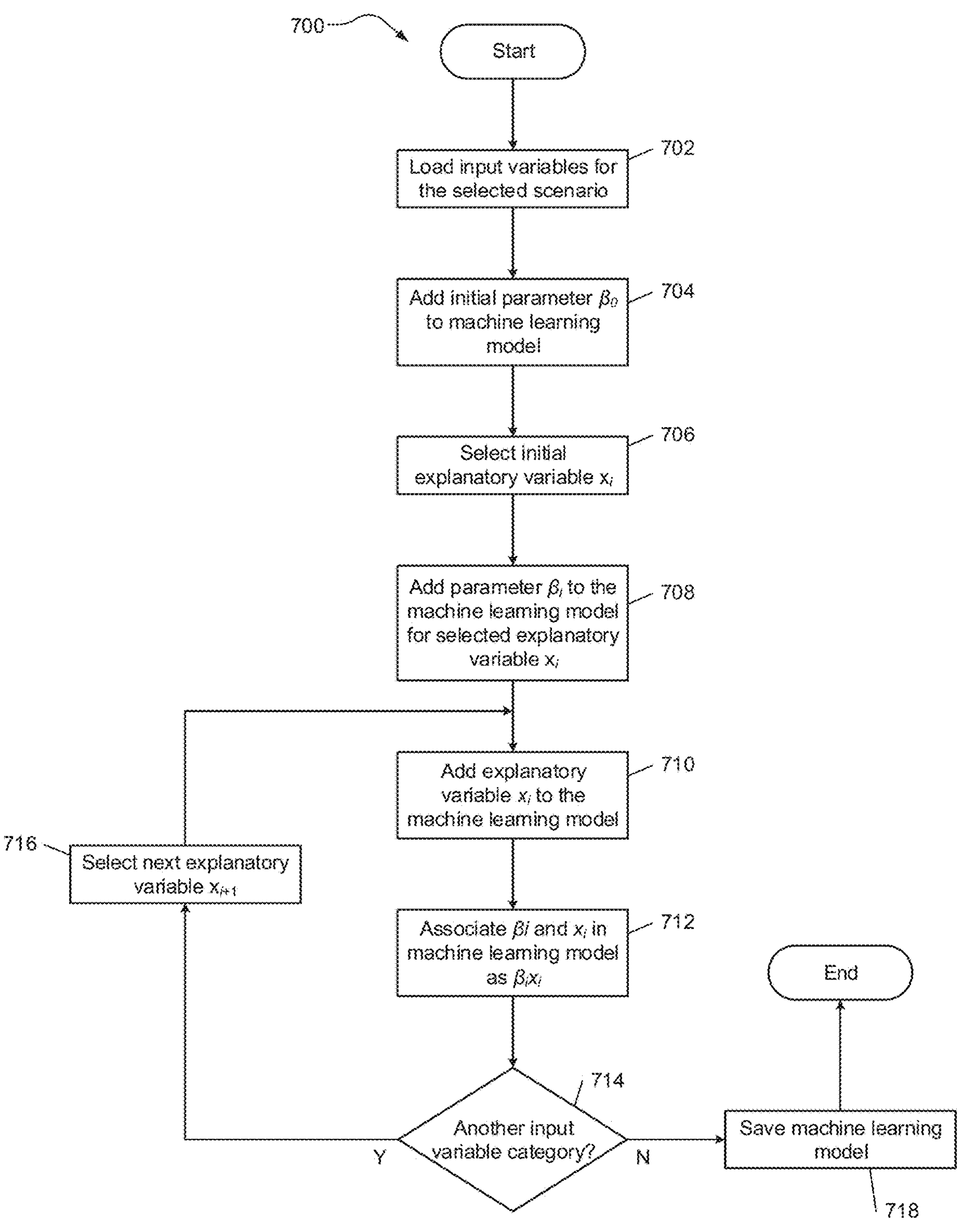
FIG. 7 is a flowchart of an example process for building a machine learning model.

FIG. 7 is a flowchart of an example process 700 which may be performed by the prediction module 416 of FIG. 4 to build a machine learning model at step 504 of process 500 of FIG. 5. At 702, control loads input variables appropriate to the scenario. In various implementations, if the selected scenario is the first scenario, control may load the input or explanatory variables from Table 1 below:

TABLE 1

| i | Description | Explanatory Variable |
|---|---|---|
| 1 | Numerical rating of symptoms related to shortness of breath experienced upon exertion over a time period | $x_1$ |
| 2 | Numerical rating of symptoms related to chest pains or palpitations experienced over the time period | $x_2$ |
| 3 | Whether the member is an integrated member (e.g., value 1) or a direct member (e.g., value 0) | $x_3$ |
| 4 | Numerical rating of symptoms related to shortness of breath at rest experienced over the time period | $x_4$ |
| 5 | Numerical rating of other symptoms related to shortness of breath upon exertion experienced over the time period | $x_5$ |
| 6 | Numerical rating of other symptoms related to shortness of breath at rest experienced over the time period | $x_6$ |

In various implementations, if the selected scenario is the second scenario, control may load the input or explanatory variables from Table 2 below:

TABLE 2

| i | Description | Explanatory Variable |
|---|---|---|
| 1 | Numerical rating of symptoms related to chest pains or palpitations experienced over the time period | $x_1$ |
| 2 | Numerical rating of symptoms related to shortness of breath experienced upon exertion over a time period | $x_2$ |
| 3 | Whether the member is an integrated member (e.g., value 1) or a direct member (e.g., value 0) | $x_3$ |
| 4 | Numerical rating of other symptoms related to chest pains or palpitations experienced over the time period | $x_4$ |
| 5 | Whether the member has been hospitalized (e.g, value 1) or not hospitalized (e.g, value 0) since the member's last contact with the pharmacy | $x_5$ |

After the appropriate explanatory variables have been loaded for the selected scenario, control proceeds to 704. At 704, an initial parameter $\beta_0$ may be added to the machine learning model. In various implementations, the machine learning model may be a logistic regression model, and the initial parameter $\beta_0$ may be the parameter not associated with any explanatory variables. After the initial parameter has been added to the model, control proceeds to 706. At 706, control selects the initial explanatory variable $x_i$ from the loaded input variable categories. Control then proceeds to 708. At 708, control may add an i-th parameter $\beta_i$ to the machine learning model. Control then proceeds to 710, where control adds the selected explanatory variable $x_i$ to the machine learning model, and continues to 712. At 712, control associates $\beta_i$ and $x_i$ in the machine learning model as $\beta_i x_i$. Control switches to 714, where control determines whether there is another explanatory variable remaining to be added to the machine learning model. If the answer at 714 is yes, control proceeds to 716, selects the next explanatory variable $x_{i+1}$, and proceeds to 710. If at 714 the answer is no, control proceeds to 718 and saves the built machine learning model.

In various implementations, if the selected scenario is the first scenario, then the saved machine learning model may be described according to Equation (1) below, where p represents the predicted probability of the member switching from monotherapy to combination therapy within the targeted future time period, and where $x_i$ corresponds to the appropriate input variable from Table 1:

$$\log\left(\frac{p}{1-p}\right) = \beta_0 + \beta_1 x_1 + \beta_2 x_2 + \beta_3 x_3 + \beta_4 x_4 + \beta_5 x_5 + \beta_6 x_6 \quad (1)$$

In various implementations, if the selected scenario is the second scenario, then the saved machine learning model may be described according to Equation (2) below, where p represents predicted probability of the member switching from drugs which do not contain prostacyclin to one or more drugs which contain prostacyclin within the targeted future time period, and where $x_i$ corresponds to the appropriate input variable from Table 2:

$$\log\left(\frac{p}{1-p}\right) = \beta_0 + \beta_1 x_1 + \beta_2 x_2 + \beta_3 x_3 + \beta_4 x_4 + \beta_5 x_5 \quad (2)$$

In various implementations, the logarithmic functions of Equation (1) and/or Equation (2) may be a natural logarithm.

Figure 8:
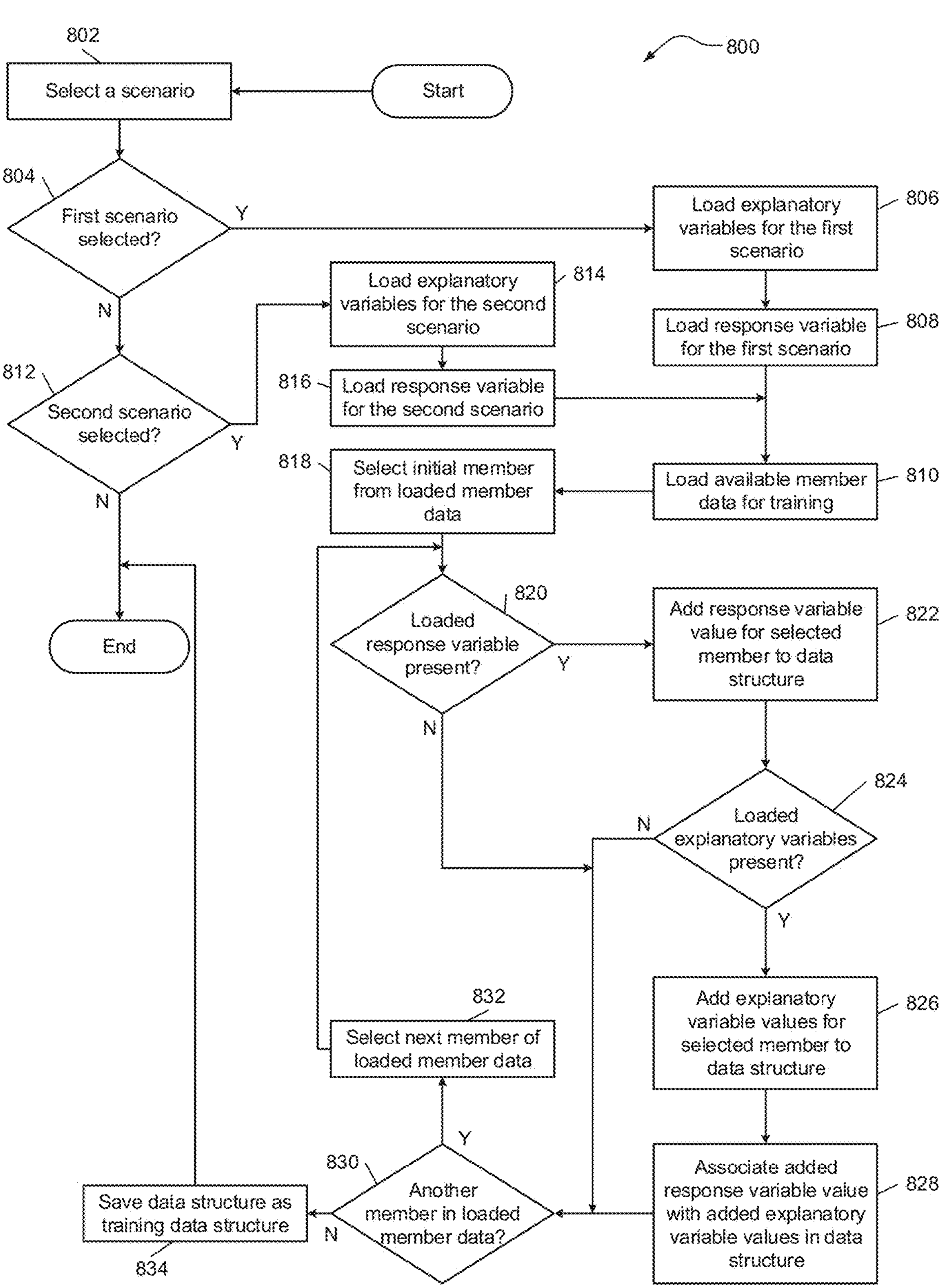
FIG. 8 is a flowchart of an example process for creating a training data structure.

FIG. 8 is a flowchart of an example process 800 which may be performed by the data sorting module 414 and/or the prediction module 416 of FIG. 4 to create a training data structure at step 506 of process 500 of FIG. 5. At 802, control may select a scenario. In various implementations, control may select the first scenario or the second scenario. In various implementations, a second scenario may be predicting the probability of one or more members switching from drugs that do not contain prostacyclin to one or more drugs which contain prostacyclin within the targeted future time period. After the appropriate scenario is selected, control proceeds to 804.

At 804, control determines whether the first scenario was selected. If the first scenario was selected, control proceeds to load explanatory variables for the first scenario at 806. In various implementations, the explanatory variables for the first scenario may be the explanatory variables previously described at Table 1. Control then proceeds to 808. At 808, control loads a response variable for the first scenario. In various implementations, the response variable for the first scenario may be whether or not a member switched from monotherapy to combination therapy within a fifth historical time period. For example, if the member switched from monotherapy to combination therapy, the response variable might have a value of "1." Otherwise, if the member did not switch, the response variable might have a value of "0." In various implementations, the fifth historical time period may be about 30 days, about 45 days, about 90 days, about 120 days, or about 365 days. In various implementations, the fifth historical time period may be about one month, about two months, about three months, about four months, about five months, about six months, about nine months, or about one year. In various implementations, the fifth historical time period may be in a range of about one day to about 365 days. In various implementations, the response variable may be loaded from member data 120. Control switches to 810.

If at 804, control determines that the first scenario was not selected, control proceeds to 812, where control determines whether the second scenario was selected. If at 812, control determines that the second scenario was selected, control proceeds to 814 and loads the explanatory variables for the second scenario. In various implementations, the explanatory variables for the second scenario may be the explanatory variables previously described at Table 2. Control then proceeds to 816. At 816, control loads a response variable for the second scenario. In various implementations, the response variable for the second scenario may be whether or not a member switched from treatment with drugs which do not contain prostacyclin to one or more drugs which contain prostacyclin within the fifth historical time period. For example, if the member switched from drugs which to do not contain prostacyclin to one or more drugs which contain prostacyclin, the response variable might have a value of "1." Otherwise, if the member did not switch, the response variable might have a value of "0." In various embodiments, the response variable might be loaded from member data 120. Control then proceeds to 810.

At 810, control loads available data from member data 120 for training, and proceeds to 818. At 818, control selects an initial member from the loaded member data, and proceeds to 820. At 820, control determines whether the loaded response variable is present in the member data for the selected member. If the member data for the selected member contains the loaded response variable, control proceeds to 822. Otherwise, control proceeds to 830. At 822, control adds the response variable value for the selected member to a data structure and proceeds to 824. At 824, control determines whether the loaded explanatory variables are present in the member data for the selected member. If the loaded explanatory variables are present in the member data for the selected member, control proceeds to 826. Otherwise, control proceeds to 830.

At 826, control adds the explanatory variable values for the selected member to the data structure and proceeds to 828. At 828, control associates the added response variable value with the added explanatory variable values in the data structure. Control proceeds to 830. At 830, control determines whether another member which was not previously selected is present in the member data. If control determines another member is present, control proceeds to 832 and selects the next member from the loaded member data. Control then proceeds to 820. If at 830, control determines that no unselected members are present in the loaded member data, control proceeds to 834, where control saves the data structure as a training data structure. An example of the saved data structure is shown below in Table 3:

TABLE 3

| Explanatory Variable Value | Response Variable Value |
|---|---|
| $x_{1, MEMBER\ 1}$ | 0 or 1 |
| $x_{2, MEMBER\ 1}$ | 0 or 1 |
| $x_{3, MEMBER\ 1}$ | 0 or 1 |
| $x_{4, MEMBER\ 1}$ | 0 or 1 |
| $x_{5, MEMBER\ 1}$ | 0 or 1 |
| $x_{6, MEMBER\ 1}$ | 0 or 1 |
| . . . | . . . |
| $x_{1, MEMBER\ n}$ | 0 or 1 |
| $x_{2, MEMBER\ n}$ | 0 or 1 |
| $x_{3, MEMBER\ n}$ | 0 or 1 |
| $x_{4, MEMBER\ n}$ | 0 or 1 |

TABLE 3-continued

| Explanatory Variable Value | Response Variable Value |
|---|---|
| $x_{5, MEMBER\ n}$ | 0 or 1 |
| $x_{6, MEMBER\ n}$ | 0 or 1 |

Table 3 represents a training data structure built where the first scenario was selected, and there are a total of n members within the available member data for training. For each member, the relevant explanatory variable from Table 1 is loaded and added to the training data structure as numerical explanatory variable value $x_i$, and each explanatory variable value $x_i$ is associated with a numerical response variable value 0 or 1. In various implementations, the response variable indicates whether or not member n switched from monotherapy to combination therapy within the fifth time period. An analogous example of a saved data structure for the second scenario is shown below in Table 4:

TABLE 4

| Explanatory Variable Value | Response Variable Value |
|---|---|
| $x_{1, MEMBER\ 1}$ | 0 or 1 |
| $x_{2, MEMBER\ 1}$ | 0 or 1 |
| $x_{3, MEMBER\ 1}$ | 0 or 1 |
| $x_{4, MEMBER\ 1}$ | 0 or 1 |
| $x_{5, MEMBER\ 1}$ | 0 or 1 |
| . . . | . . . |
| $x_{1, MEMBER\ n}$ | 0 or 1 |
| $x_{2, MEMBER\ n}$ | 0 or 1 |
| $x_{3, MEMBER\ n}$ | 0 or 1 |
| $x_{4, MEMBER\ n}$ | 0 or 1 |
| $x_{5, MEMBER\ n}$ | 0 or 1 |

Table 4 represents a training data structure built where the second scenario was selected, and there are a total of n members within the available member data for training. For each member, the relevant explanatory variable from Table 2 is loaded and added to the training data structure as a numerical explanatory variable value $x_i$, and each explanatory variable value $x_i$ is associated with a numerical response variable value 0 or 1. In various implementations, the explanatory variable indicates whether or not member n switched from drugs which to do not contain prostacyclin to one or more drugs which contain prostacyclin within the fifth historical time period.

Figure 9:
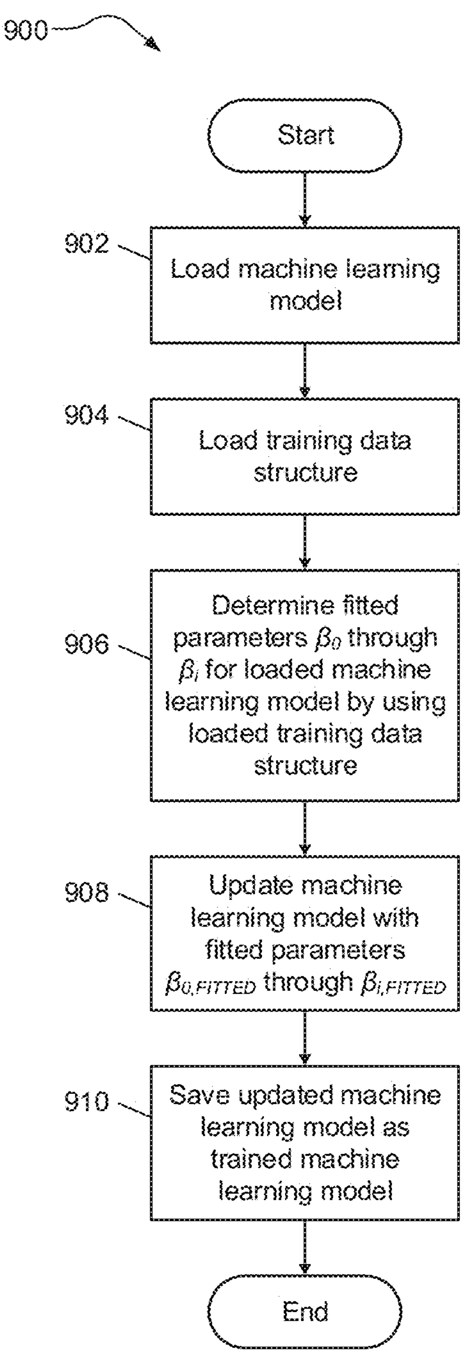
FIG. 9 is a flowchart of an example process for training a machine learning model.

FIG. 9 is a flowchart of an example process 900 which may be performed by the prediction module 416 of FIG. 4 to train the machine learning model at step 508 of process 500 of FIG. 5. At step 902, control may load the machine learning model saved at step 718 of process 700. In various implementations, if the first scenario is selected, the machine learning model defined by Equation (1) may be loaded. In various implementations, if the second scenario is selected, the machine learning model defined by Equation (2) may be loaded. Control proceeds to 904. At 904, control may load the training data structure saved at step 834 of process 800. For example, if the first scenario is selected, the training data structure of Table 3 may be loaded, or if the second scenario is selected, the training data structure of Table 4 may be loaded. After the training data structure is loaded, control proceeds to 906.

At 906, control determines best fits for each of the parameters $\beta_0$ through $\beta_i$ of the machine learning model of Equation (1) or Equation (2). In various implementations, the training data structure may be represented on a scatter plot. The numerical explanatory variable values may be plotted on the independent axis, while the response variable values may be plotted on the dependent axis. According to the machine learning models of Equations (1) and (2), the log odds $$\log\left(\frac{p}{1-p}\right)$$

of the output probability p is modeled as a linear function of explanatory variables $x_1$ through $x_i$. Thus, a fitted sigmoid function, such as a fitted logistic function may be used to model the predicted output p. In various implementations, an algorithm such as a maximum-likelihood estimation algorithm may be used to fit the parameters $\beta_0$ through $\beta_i$ of the sigmoid function to the training data structure. In various implementations, the gradient descent algorithm, Broyden-Fletcher-Goldfarb-Shanno (BFGS) algorithm, limited-memory BFGS algorithm, or conjugate gradient algorithm may be used. At 908, if under the first scenario, the machine learning model of Equation (1) may be updated to Equation (3) below, where $\beta_{i,FITTED}$ represented a fitted parameter:

$$\log\left(\frac{p}{1-p}\right) = \beta_{0,FITTED} + \beta_{1,FITTED}x_1 + \beta_{2,FITTED}x_2 + \beta_{3,FITTED}x_3 + \beta_{4,FITTED}x_4 + \beta_{5,FITTED}x_5 + \beta_{6,FITTED}x_6 \tag{3}$$

Similarly, if under the second scenario, the machine learning model of Equation (2) may be updated to Equation (4) below:

$$\log\left(\frac{p}{1-p}\right) = \beta_{0,FITTED} + \beta_{1,FITTED}x_1 + \beta_{2,FITTED}x_2 + \beta_{3,FITTED}x_3 + \beta_{4,FITTED}x_4 + \beta_{5,FITTED}x_5 + \beta_{6,FITTED}x_6 \tag{4}$$

The updated machine learning models of Equation (3) or Equation (4) may be saved a trained machine learning model at 910.

Figure 10:
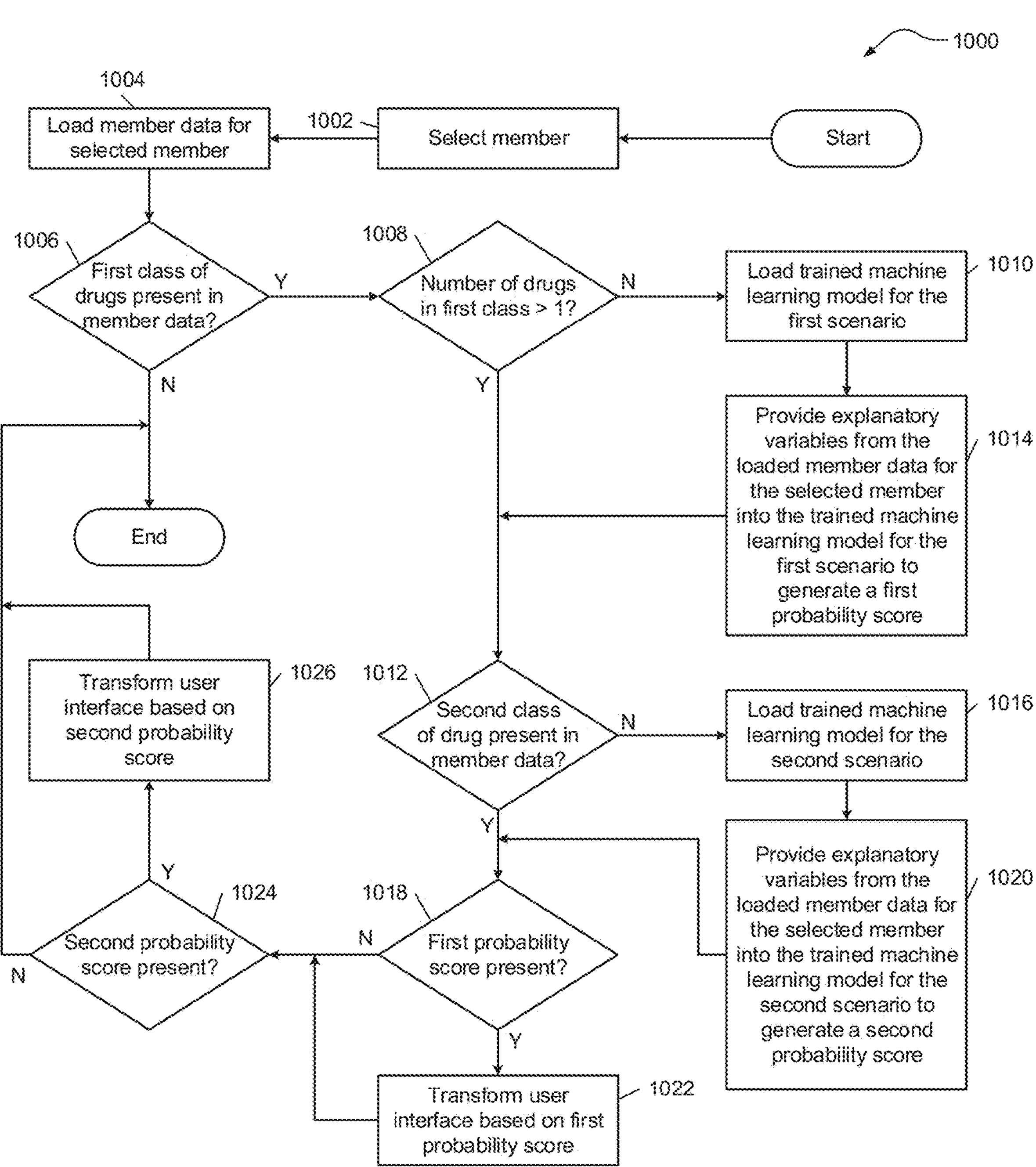
FIG. 10 is a flowchart of an example process for predicting a single-member-switch probability and transforming a user interface accordingly.

FIG. 10 is a flowchart of an example process 1000 which may be performed by the prediction module 416 and the user interface transformation module 136 of FIG. 4 to predict a probability of a single member switching using the trained machine learning model at step 510 and transform the user interface at step 512 of process 500 of FIG. 5. In various implementations, process 1000 may automatically determine whether the first scenario or the second scenario is the appropriate scenario. Control begins in response to a user selecting a member on a user interface. For example, the user may select a member on a user interface generated by the user interface transformation module 136 of the web portal 132. Control proceeds to 1002, where control accesses the member data 120 stored on the storage device 110 through the access module 134 and network 104 and selects the corresponding member. After the appropriate member is selected, control proceeds to 1004, where control loads the member data of the selected member from member data 120. Control proceeds to 1006. At 1006, control determines whether any of the first class of drugs is present in the member data of the selected member. The first class of drugs may be any of the drugs previously discussed with respect to process 600. If at least one of the first class of drugs is present, control proceeds to 1008, where control determines if more than one drug of the first class is present in the member history. If at 1008, control determines that only one drug of the first class is present in the member history, control proceeds to 1010. If at 1008, control determines that more than one drug of the first class is present in the member history, control proceeds to 1012.

At 1010, control loads the trained machine learning model for the first scenario. For example, control may load the trained machine learning model described by Equation (3). Control proceeds to 1014. At 1214, control loads the relevant numerical explanatory variables $x_1$ through $x_i$ for the loaded trained machine learning model from the member data for the selected member, and provides the explanatory variables to the trained machine learning model to generate a first probability score $p_1$. In various implementations, the first probability score $p_1$ represents a likelihood that the selected member will switch from monotherapy treatment for pulmonary arterial hypertension to combination therapy within the targeted future time period. Control proceeds to 1012.

At 1012, control determines whether any of the second class of drugs is present in the member history of the selected member. The second class of drugs may be any of the drugs previously discussed with respect to process 600. If the second class of drugs is not present in the member history, control proceeds to 1016. Otherwise, if the second class of drugs is present in the member history, control proceeds to 1018. At 1016, control loads the trained machine learning model for the second scenario. For example, control may load the trained machine learning model described by Equation (4). Control proceeds to 1020.

At 1020, control loads the relevant numerical explanatory variables $x_1$ through $x_i$ for the loaded trained machine learning model from the member data for the selected member, and provides the explanatory variables to the trained machine learning model to generate a second probability score $p_2$. In various implementations, the second probability score $p_2$ represents a likelihood that the selected member will switch from treatment for pulmonary arterial hypertension with drugs which do not contain prostacyclin to treatment with at least one drug containing prostacyclin within the targeted future time period. Control proceeds to 1018.

At 1018, control determines whether the first probability score $p_1$ has been generated. If the first probability score $p_1$ has been generated, control proceeds to 1022, where the user interface transformation module 136 transforms the user interface according to the first probability score $p_1$. For example, the user interface transformation module 136 may display the relevant member data along with the first probability score $p_1$ on a screen of the user device 108. In various implementations, the user interface transformation module 136 may display an explanation that the first scenario is appropriate to the selected member.

If at 1018, control determines that the first probability score $p_1$ has not been generated, control proceeds instead to 1024, where control determines whether the second probability score $p_2$ has been generated. If at 1024, control determines that the second probability score $p_2$ has been generated, control proceeds to 1026, where the user interface transformation module 136 transforms the user interface according to the second probability score $p_2$. For example, the user interface transformation module 136 may display the relevant member data along with the second probability score $p_2$ on the screen of the user device 108. In various implementations, the user interface transformation module 136 may display an explanation that the second scenario is appropriate to the selected member.

Figure 11:
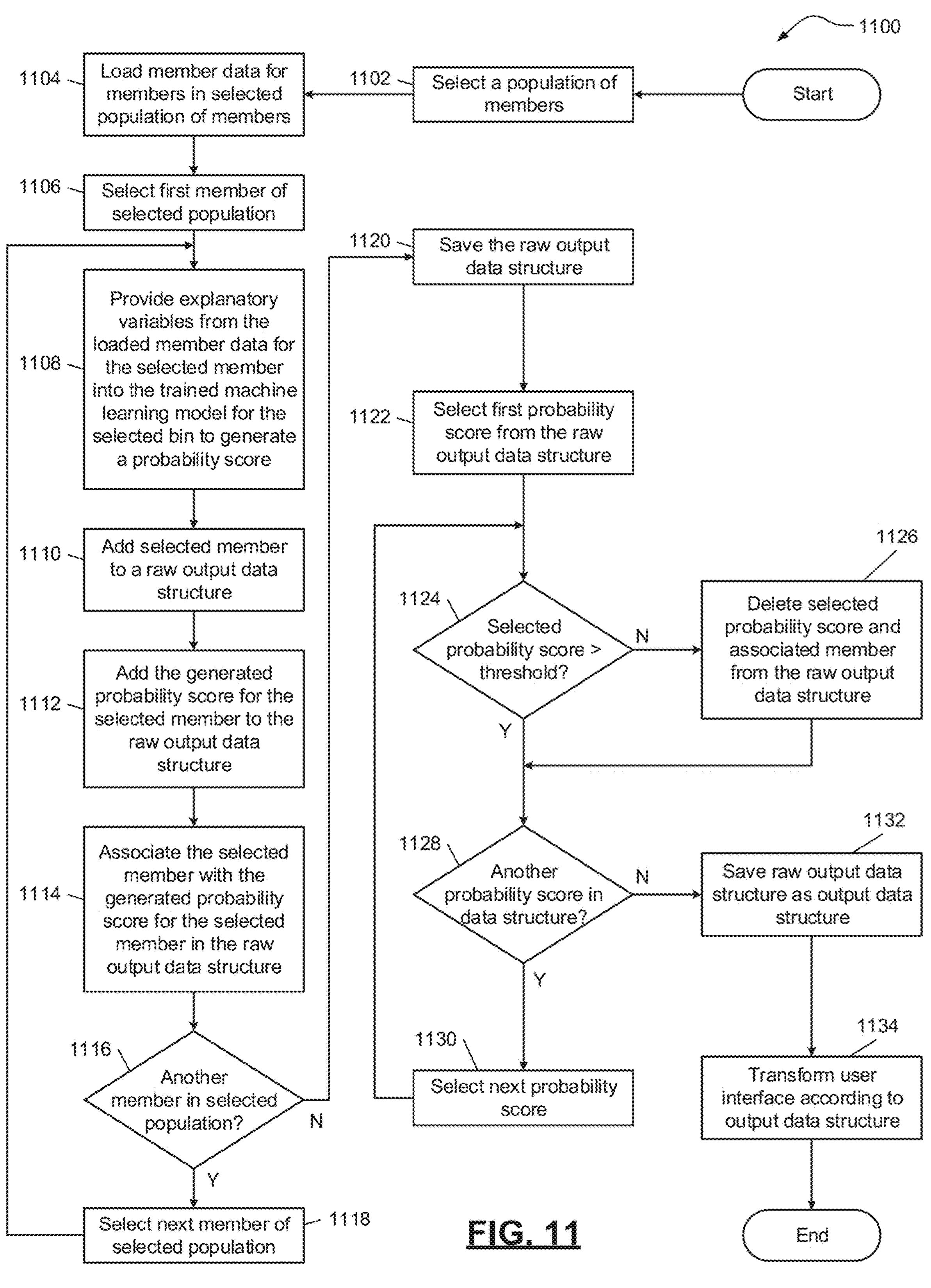
FIG. 11 is a flowchart of an example process for predicting a multiple-member-switch probability and transforming a user interface accordingly.

FIG. 11 is a flowchart of an example process 1100 which may be performed by the prediction module 416 and the user interface transformation module 136 of FIG. 4 to predict probabilities of multiple members switching treatments using the trained machine learning model at step 510 and transform the user interface at step 512 of process 500 of FIG. 5. In various implementations, it may be desirable to perform automated bulk analysis on an entire population of members in order to determine which, if any, of the members may be likely to transition from one form of therapy to another within the targeted future time period.

Control begins in response to the user selecting a population of members for analysis under the first scenario or the second scenario. At 1102, control selects the relevant population of members from the member data 120, and proceeds to 1104. At 1104, control loads member data for each of the members in the selected population of members. Control proceeds to 1106.

At 1106, control selects the first member of the selected population of members. Control proceeds to 1108. At 1108, control provides the relevant input variables numerical explanatory variables $x_1$ through $x_i$ for the relevant scenario into the relevant trained machine learning model for the selected bin to generate a probability score for the selected member. Control proceeds to 1110, where control adds the selected member to a raw output data structure. After 1110, control proceeds to 1112, where control adds the probability score generated at 1108 for the selected member to the raw output data structure. Control proceeds to 1114.

At 1114, control associates the selected member with the generated probability score for the selected member in the raw output data structure. Control continues to 1116, where control determines whether there is another member in the selected population which has not yet been parsed. If there are additional members in the selected population which have not been parsed, control proceeds to 1118 and selects the next member of the selected population and continues to 1108. If at 1116 there are no additional members in the selected population left to be parsed, control proceeds to 1120.

At 1120, control saves the raw output data structure and proceeds to 1122. At 1122, control selects the first probability score from the raw output data structure. Control proceeds to 1124. At 1124, control determines whether the selected probability score is greater than a threshold. If the selected probability score is not greater than the threshold, control proceeds to 1126. In various implementations, the threshold may be about 0.0920. In various implementations, the threshold may be in a range of about 0.0920 to about 1.0. In various implementations, the threshold may be about 0.0497. In various implementations, the threshold may be in a range of about 0.0497 to about 1.0. At 1126, control deletes the selected probability score and the associated member from the raw output data structure. Control proceeds to 1128.

If at 1124, control determines the selected probability score is greater than the threshold, control proceeds to 1128. At 1128, control determines whether there is another unanalyzed probability score remaining in the data structure. If at 1128, the answer is yes, control proceeds to select the next probability score at 1130, and proceeds to 1124. If at 1128, the data structure does not contain another unanalyzed probability score, control proceeds to 1132. At 1132, the raw output structure is saved as the output data structure. Control continues to 1134, the user interface transformation module 136 transforms the user interface according to the output data structure. For example, the user interface transformation module 136 may display whether the machine learning model for the first scenario and/or the second scenario was applied, and each member in the output data structure along with the member's associated probability score on the user interface.

Figure 12:
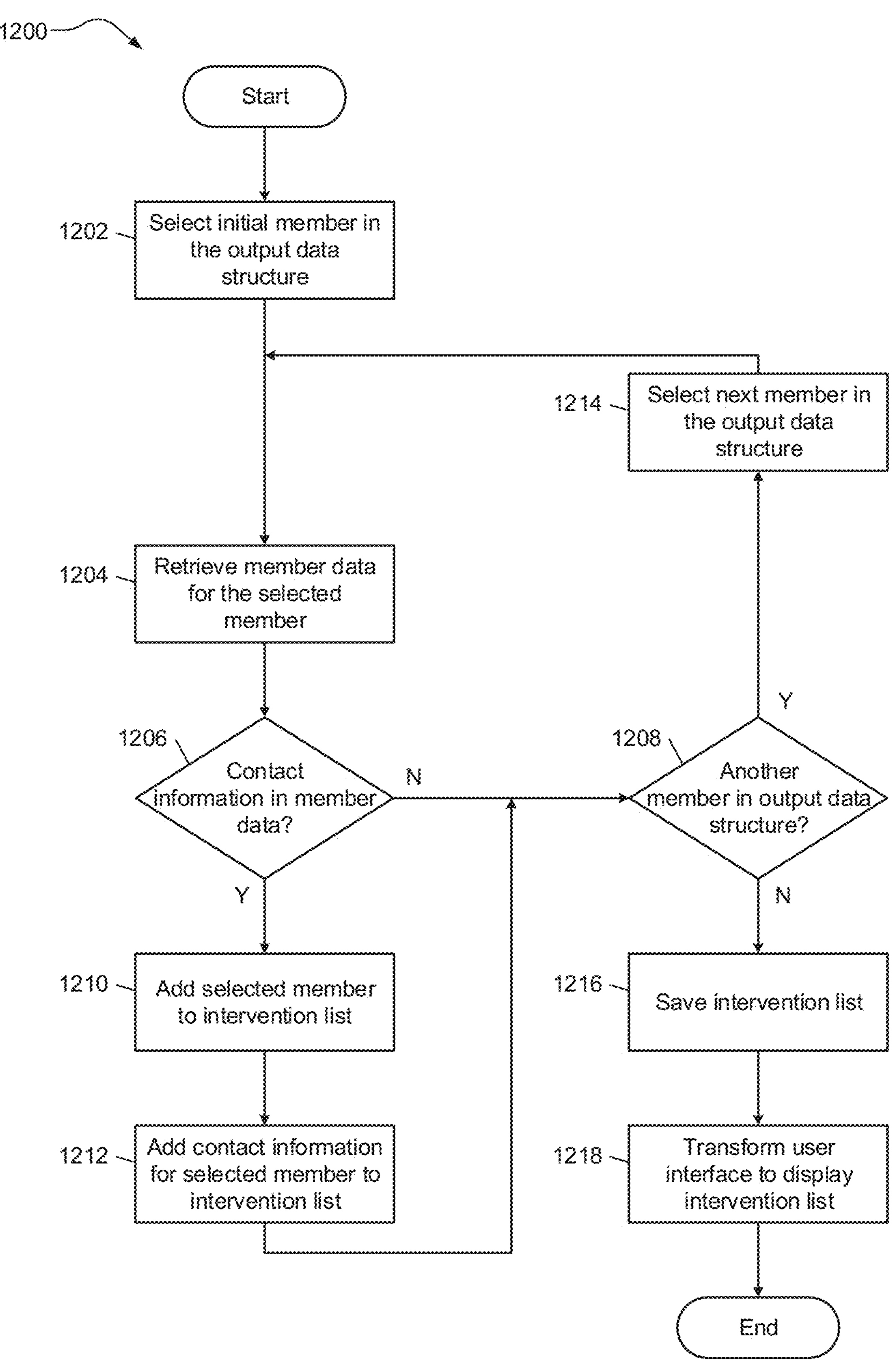
FIG. 12 is a flowchart of an example process for automatically generating an intervention list and transforming a user interface accordingly.

FIG. 12 is a flowchart of an example process 1200 which may be performed by the prediction module 416 and/or the user interface transformation module 136 of FIG. 4 to transform the user interface according to the output data structure at step 1134 of process 1100 of FIG. 11. In various implementations, it may be desirable to automatically generate one or more intervention lists in order to facilitate clinical teams' performing outreach to selected members. Control begins at 1202. At 1202, control selects an initial member from the output data structure. Control proceeds to 1204. At 1204, control retrieves the member data 120 for the selected member from storage device 110. Control proceeds to 1206. At 1206, control determines whether contact information (e.g., mailing addresses, telephone numbers, and/or e-mail addresses) is present in the retrieved member data 120. If at 1206, control determines that contact information is present, control proceeds to 1208. Otherwise, control proceeds to 1210.

At 1208, control adds the selected member to the intervention list. Control proceeds to 1212. At 1212, control adds the contact information for the selected member retrieved from member data 120 to the intervention list and associated the contact information with the selected member. Control proceeds to 1210. At 1210, control determines whether another member is present in the output data structure. If at 1210, control determines that another member is present, control proceeds to 1214. Otherwise, control proceeds to 1216. At 1214, control selects the next member in the output data structure and proceeds back to 1204. At 1216, control saves the intervention list and proceeds to 1218. At 1218, control transforms the user interface to display the intervention list. In various implementations, the contact information of each member on the intervention list may be displayed with the name and/or personal identifier(s) of the member on the user interface.

Figure 13:
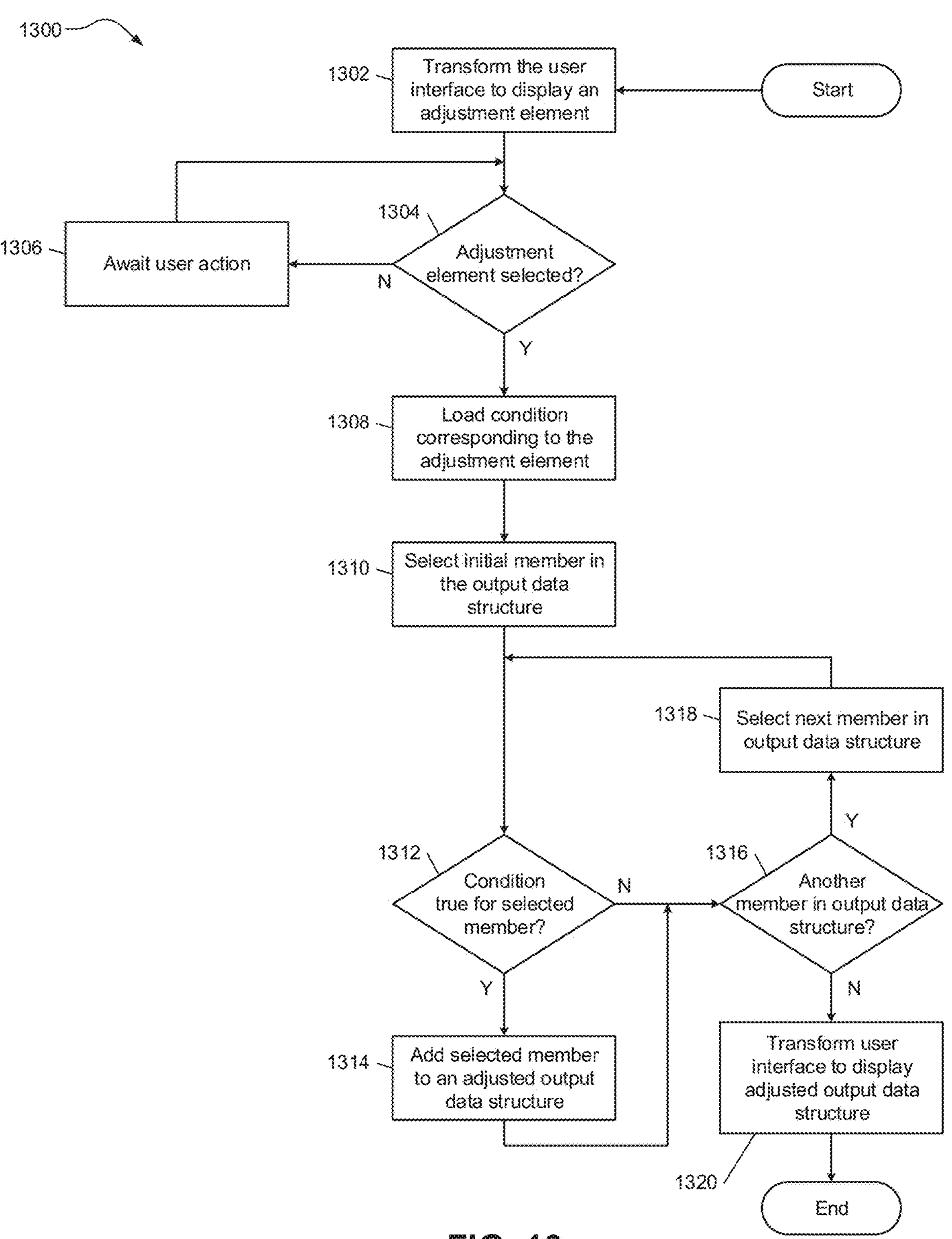
FIG. 13 is a flowchart of an example process for automatically filtering a data structure according to one or more conditions and transforming a user interface accordingly.

FIG. 13 is a flowchart of an example process 1300 which may be performed by the prediction module 416 and/or the user interface transformation module 136 of FIG. 4 to transform the user interface according to the output data structure at step 1134 of process 1100 of FIG. 11. In various implementations, the output data structure may be further refined or filtered according to one or more conditions, such as clinical rules or other heuristics. Control begins at 1302. At 1302, control transforms the user interface to display an adjustment element. In various implementations, the adjustment element may be a selectable element corresponding to one or more conditions. For example, condition may be a patient having a mean pulmonary artery pressure of greater than or equal to 25 mmHg at rest. By selecting the adjustment element, control refines the output data structure by automatically filtering out all members having a mean pulmonary arterial pressure of less than 25 mmHg at rest. Control proceeds to 1304.

At 1304, control determines whether the adjustment element has been selected. If at 1304, the adjustment element has not been selected, control proceeds to 1306. Otherwise, if the adjustment element has been selected, control proceeds to 1308. At 1306, control awaits user action, and returns to 1304. At 1308, control loads the condition corresponding to the adjustment element. For example, if the condition corresponding to the adjustment element is patient having a mean pulmonary artery pressure of less than 25 mmHg at rest, control loads a rule corresponding to the condition. For example, control may load the rule:

mean pulmonary arterial pressure>=25 mmHg

Control proceeds to 1310. At 1310, control selects an initial member from the output data structure and loads member data 120 for the selected member. In various implementations, the member data 120 may contain medical records or a clinical history of the selected member. Control proceeds to 1312. At 1312, control determines whether the condition is true for the selected member by applying the rule to the member data 120 for the selected member. For example, if the member data 120 for the selected member indicates that the member has had a mean pulmonary arterial pressure of greater than or equal to 25 mmHg, then control may determine the condition to be true. If, at 1312, control determines the condition to true, control proceeds to 1314. Otherwise, control proceeds to 1316.

At 1314, control adds the selected member to an adjusted output data structure. Control proceeds to 1316. At 1316, control determines whether another member is present in the output data structure. If control determines that another member is present in the output data structure, control proceeds to 1318; otherwise, control proceeds to 1320. At 1318, control selects the next member in the output data structure and returns to 1312. At 1320, control transforms the user interface to display the adjusted output data structure.

Conclusion

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. In the written description and claims, one or more steps within a method may be executed in a different order (or concurrently) without altering the principles of the present disclosure. Similarly, one or more instructions stored in a non-transitory computer-readable medium may be executed in different order (or concurrently) without altering the principles of the present disclosure. Unless indicated otherwise, numbering or other labeling of instructions or method steps is done for convenient reference, not to indicate a fixed order.

Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements.

The phrase "at least one of A, B, and C" should be construed to mean a logical (A OR B OR C), using a non-exclusive logical OR, and should not be construed to mean "at least one of A, at least one of B, and at least one of C." The term "set" does not necessarily exclude the empty set—in other words, in some circumstances a "set" may have zero elements. The term "non-empty set" may be used to indicate exclusion of the empty set—in other words, a non-empty set will always have one or more elements. The term "subset" does not necessarily require a proper subset. In other words, a "subset" of a first set may be coextensive with (equal to) the first set. Further, the term "subset" does not necessarily exclude the empty set—in some circumstances a "subset" may have zero elements.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2020 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module. For example, the client module may include a native or web application executing on a client device and in network communication with the server module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. Such apparatuses and methods may be described as computerized apparatuses and computerized methods. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A computerized method for transforming a user interface according to machine learning, the computerized method comprising:

selecting a persona from a data store;

loading, into a data processing module, a data structure associated with the selected persona;

determining, at the data processing module, whether a first condition of a set of conditions is true for the data structure;

in response to determining that the first condition is true for the data structure, determining whether a second condition of the set of conditions is true for the data structure;

in response to determining that the second condition is not true for the data structure:

building, at the data processing module, a first trained machine learning model by:

loading, at the data processing module, a first initial parameter, a first set of explanatory variables from the data structure, and a first response variable, adding the first initial parameter and the first set of explanatory variables to a first training data structure, determining whether the first response variable is present in the data structure, in response to determining that the first response variable is present in the data structure:

adding a first value from the data structure associated with the first response variable to the first training data structure, and associating the first value and the first set of explanatory variables in the first training data structure, and training the first trained machine learning model with the first training data structure, inputting, at the data processing module, the first set of explanatory variables to the first trained machine learning model to generate a first event prediction, wherein the first event prediction includes a probability of a first event occurring within a first epoch, and transforming the user interface according to the selected persona and the first event prediction;

in response to determining that the second condition is true for the data structure, determining whether a third condition of the set of conditions is true for the data structure; and in response to determining that the third condition is true for the data structure:

building, at the data processing module, a second trained machine learning model by:

loading, at the data processing module, a second initial parameter, a second set of explanatory variables from the data structure, and a second response variable, adding the second initial parameter and the second set of explanatory variables to a second training data structure, determining whether the second response variable is present in the data structure, in response to determining that the second response variable is present in the data structure:

adding a second value from the data structure associated with the second response variable to a second training data structure, and associating the second value and the second set of explanatory variables in the second training data structure, and training the second trained machine learning model with the second training data structure, inputting, at the data processing module, the second set of explanatory variables to the second trained machine learning model to generate a second event prediction, wherein the second event prediction includes a probability of a second event occurring within a second epoch, and transforming the user interface according to the selected persona and the second event prediction, wherein the first event prediction is a probability of the selected persona transitioning from treatment with a single drug from a first class of drugs to multiple drugs from the first class of drugs within a first epoch.

2. The computerized method of claim 1, wherein the second event prediction is a probability of the selected persona transitioning from treatment with a drug not containing a compound to a drug containing the compound within a second epoch.

3. The computerized method of claim 2, wherein the first condition is a presence of at least one drug of the first class of drugs in the data structure.

4. The computerized method of claim 3, wherein the second condition is a presence of more than one drug of the first class of drugs in the data structure.

5. The computerized method of claim 4, wherein the third condition is a presence of the compound in the data structure.

6. The computerized method of claim 5, wherein the first trained machine learning model is a first multiple logistic regression model.

7. The computerized method of claim 6, wherein the second trained machine learning model is a second multiple logistic regression model.

8. The computerized method of claim 7, wherein the first class of drugs comprises drugs associated with treating pulmonary arterial hypertension.

9. The computerized method of claim 8, wherein the compound comprises prostacyclin.

10. The computerized method of claim 2, wherein the second set of explanatory variables includes:

a numerical rating of symptoms related to chest pains or palpitations experienced over the second epoch, a numerical rating of symptoms related to shortness of breath experienced upon exertion over the second epoch, a value indicative of whether a member associated with the selected persona is an integrated member or a direct member, a numerical rating of other symptoms related to chest pains or palpitations experienced over the second epoch, and a value indicative of whether the member has been hospitalized.

11. The computerized method of claim 1, wherein the first set of explanatory variables includes:

a numerical rating of symptoms related to shortness of breath experienced upon exertion over the first epoch, a numerical rating of symptoms related to chest pains or palpitations experienced over the first epoch, a value indicative of whether a member associated with the selected persona is an integrated member or a direct member, a numerical rating of symptoms related to shortness of breath at rest experienced over the first epoch, a numerical rating of other symptoms related to shortness of breath upon exertion experienced over the first epoch, and a numerical rating of other symptoms related to shortness of breath at rest experienced over the first epoch.

12. The computerized method of claim 1, further comprising:

in response to determining that the first condition is true for the data structure, copying the selected persona and the data structure into a first bin, in response to determining that the second condition is not true for the data structure, copying the selected persona and the data structure into a second bin, in response to determining that the second condition is true for the data structure, copying the selected persona and the data structure into a third bin, in response to determining that the third condition is not true for the data structure, copying the selected persona and the data structure into a fourth bin, in response to determining that the third condition is true for the data structure, copying the selected persona and the data structure into a fifth bin, wherein:

the first event prediction includes a probability of the selected persona transitioning from the second bin to a third bin within a first epoch, and the second event prediction includes a probability of the selected persona transitioning from the fifth bin to a sixth bin within a second epoch.

13. A system for transforming a user interface according to machine learning, the system comprising:

a first data store including a persona and a data structure associated with the persona;

a second data store configured to store:

at least one of a first trained machine learning model and a second trained machine learning model, and at least one of a first set of explanatory variables and a second set of explanatory variables; and at least one processor operatively coupled to the first data store and the second data store, wherein the at least one processor is configured by a set of instructions to:

determine whether a first condition of a set of conditions is true for the data structure, in response to determining that the first condition is true for the data structure, determine whether a second condition of the set of conditions is true for the data structure, in response to determining that the second condition is not true for the data structure:

build the first trained machine learning model by:

adding a first initial parameter and the first set of explanatory variables to a first training data structure, determining whether a first response variable is present in the data structure, in response to determining that the first response variable is present in the data structure:

adding a first value from the data structure associated with the first response variable to the first training data structure, and associating the first value and the first set of explanatory variables in the first training data structure, and training the first trained machine learning model with the first training data structure, input the first set of explanatory variables into the first trained machine learning model and generate a first event prediction, wherein the first event prediction includes a probability of a first event occurring within a first epoch, and transform the user interface according to the first event prediction, in response to determining that the second condition is true for the data structure, determine whether a third condition of the set of conditions is true for the data structure; and in response to determining that the third condition is true for the data structure:

build the second trained machine learning model by:

adding a second initial parameter and the second set of explanatory variables to a second training data structure, determining whether a second response variable is present in the data structure, in response to a determination that the second response variable is present in the data structure:

adding a second value from the data structure associated with the second response variable to a second training data structure, and associating the second value and the second set of explanatory variables in the second training data structure, and training the second trained machine learning model with the second training data structure, input the second set of explanatory variables into the second trained machine learning model to generate a second event prediction, wherein the second event prediction includes a probability of a second event occurring within a second epoch, and transform the user interface according to the second event prediction, wherein the first event prediction is a probability of the persona transitioning from treatment with a single drug in a first class of drugs to treatment with multiple drugs in the first class of drugs within a first epoch.

14. The system of claim 13, wherein the second event prediction is a probability of the persona transitioning from treatment with a drug not containing a compound to treatment with a drug containing the compound within a second epoch.

15. The system of claim 14, wherein the first condition is a presence of at least one drug of the first class of drugs in the data structure.

16. The system of claim 15, wherein the second condition is a presence of more than one drug of the first class of drugs in the data structure.

17. The system of claim 16, wherein the second condition is a presence of the compound in the data structure.

18. The system of claim 17, wherein:

the first trained machine learning model is a first multiple logistic regression model; and the second trained machine learning model is a second multiple logistic regression model.

19. A non-transitory computer-readable medium comprising executable instructions for transforming a user interface according to machine learning, wherein the executable instructions include:

selecting a persona from a data store;

loading, into a data processing module, a data structure associated with the selected persona;

determining, at the data processing module, whether a first condition of a set of conditions is true for the data structure;

in response to determining that the first condition is true for the data structure, determining whether a second condition of the set of conditions is true for the data structure;

in response to determining that the second condition is not true for the data structure:

building, at the data processing module, a first trained machine learning model by:

loading, at the data processing module, a first initial parameter, a first set of explanatory variables from the data structure, a first response variable, adding the first initial parameter and the first set of explanatory variables to a first training data structure, determining whether the first response variable is present in the data structure, in response to determining that the first response variable is present in the data structure:

adding a first value from the data structure associated with the first response variable to the first training data structure, and associating the first value and the first set of explanatory variables in the first training data structure, and training the first trained machine learning model with the first training data structure, inputting, at the data processing module, the first set of explanatory variables to the first trained machine learning model to generate a first event prediction, wherein the first event prediction includes a probability of a first event occurring within a first epoch, and transforming the user interface according to the selected persona and the first event prediction;

in response to determining that the second condition is true for the data structure, determining whether a third condition of the set of conditions is true for the data structure, wherein:

the second condition and the third condition are indicative of a second event, and the first event and the second event are different; and in response to determining that the third condition is true for the data structure:

building, at the data processing module, a second trained machine learning model by:

loading, at the data processing module, a second initial parameter, a second set of explanatory variables from the data structure, and a second response variable, adding the second initial parameter and the second set of explanatory variables to a second training data structure, determining whether the second response variable is present in the data structure, in response to determining that the second response variable is present in the data structure:

adding a second value from the data structure associated with the second response variable to the second training data structure, and associating the second value and the second set of explanatory variables in the second training data structure, and training the second trained machine learning model with the second training data structure, inputting, at the data processing module, the second set of explanatory variables to the second trained machine learning model to generate a second event prediction, wherein the second event prediction includes a probability of a second event occurring within a second epoch, and transforming the user interface according to the selected persona and the second event prediction, wherein the first event prediction is a probability of the selected persona transitioning from treatment with a single drug in a first class of drugs to treatment with multiple drugs in the first class of drugs within a first epoch.

20. The non-transitory computer-readable medium of claim 19, wherein the second event prediction is a probability of the selected persona transitioning from treatment with a drug not containing a compound to treatment with a drug containing the compound within a second epoch.

* * * * *